United States Patent [19]

Vanhoof

[11] 3,970,650

[45] July 20, 1976

[54] DERIVATIVES OF TETRALONE AND THE PREPARATION THEREOF

[75] Inventor: Pierre M. Vanhoof, Brussels, Belgium

[73] Assignee: A. Christiaens Societe Anonyme, Brussels, Belgium

[22] Filed: Sept. 16, 1975

[21] Appl. No.: 613,828

[30] Foreign Application Priority Data

Sept. 16, 1974 United Kingdom............... 40296/74

[52] U.S. Cl. ............................ 260/240 B; 424/263; 424/325; 260/294.8 C; 260/556 AR; 260/571; 260/576
[51] Int. Cl.$^2$....................................... C07D 213/50
[58] Field of Search................. 260/296 B, 571, 576

[56] References Cited
UNITED STATES PATENTS 2,647,123   7/1953   Calandra et al.................. 260/296 B

FOREIGN PATENTS OR APPLICATIONS 768,604   8/1934   France

OTHER PUBLICATIONS

Elsevier's Encyclopaedia of Organic Chemistry, vol. 12B, Series III, pp. 2653 to 2657, Elsevier Publishing Co., Inc., N.Y., (1950).

Sarkis et al., J. of Chem. & Eng. Data, vol. 18, No. 1, pp. 102 to 104, (1973).

Fries et al., Annalen der Chemie, vol. 470, pp. 20 to 37, (1929).

*Primary Examiner*—John D. Randolph
*Attorney, Agent, or Firm*—Sughrue, Rothwell, Mion, Zinn & Macpeak

[57]     ABSTRACT

New 2-R-amino-tetraline-1-ones, in which R represents a pyridyl or phenyl radical which may be substituted by a methoxy group are prepared by reacting 2-bromo-tetralone with an amine of the formula R-NH$_2$.

These new 2-R-amino-tetraline-1-ones are valuable intermediates for the preparation of pharmaceutically active compounds.

3 Claims, No Drawings

DERIVATIVES OF TETRALONE AND THE PREPARATION THEREOF

BRIEF DESCRIPTION OF THE INVENTION

This invention relates to new derivatives of tetralone or tetrahydronaphtalene-1-one, their preparation and use.

Said new derivatives are 2-R-amino-tetraline-1-ones which may be represented by the formula:

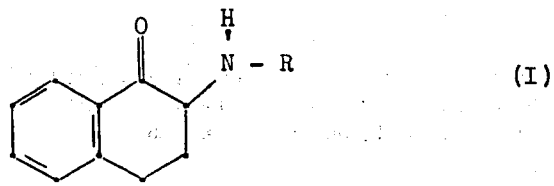

(I)

in which R represents a pyridyl or phenyl radical which may be substituted, in the ortho, meta or para position, by a methoxy group.

This invention also relates to a process for the preparation of the new 2-R-amino-tetraline-1-ones of formula I.

According to this invention the 2-R-amino-tetraline-2-ones are prepared by reacting 2-bromotetralone with an amine of the formula:

R—NH$_2$ (II)

in which R has the above meanings.

DETAILED DESCRIPTION OF THE INVENTION

The new compounds of formula (I), are obtained with a high yield when the reactants are stirred under an inert blanket at a temperature comprised between about 20°C and 60°C.

When the reactant of formula (II) is a liquid (for example, aniline), the other reactant (2-bromo-tetralone) is dissolved in it and the obtained solution is stirred under an inert blanket.

When the reactant of formula (II) is a solid, this reactant as well as the other reactant are dissolved in ether. After removal of the ether, the mixture is stirred under an inert blanket.

EXAMPLES

The process according to this invention is illustrated by the following examples 1 to 6:

EXAMPLE 1

Preparation of 2-phenylamino-tetraline-1-one (formula I;R=phenyl 0.05 mole of 2-bromotetralone is dissolved in 0.15 mole of aniline. The mixture is stirred at 35°–38°C under nitrogen blanket for 24 hours. Is then taken up with 150 ml of water and brought to pH 2 by adding hydrochloric acid. It is allowed to rest overnight in the ice box, filtered and dried. After recrystallization from the minimum amount of methanol needed for dissolving the product at the boiling point, the desired compound is obtained; m.p. 89°–92°C. Analytical sample m.p. 93°–95°C.

| Analysis | C | H | N |
|---|---|---|---|
| % calculated | 80.98 | 6.37 | 5.90 |
| % found | 80.76 | 6.38 | 5.8 |

I.R. Spectrum: NH: 3330 cm$^{-1}$; C=O: 1685 cm$^{-1}$; C—N: 1355 cm$^{-1}$ def. 1580 NH cm$^{-1}$.

N.M.R.

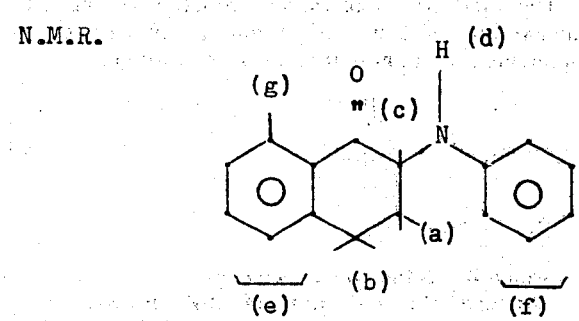

a. : massive complex δ : 2.1
b. : massive complex δ : 3.05
c. : double doublet δ : 4.1
d. : δ : 5.6 : disappears by deuteration
e. : δ : 6.65 p.p.m.
f. : δ : 7.2 p.p.m.
g. : δ : 8 p.p.m.
Yield : 80 %

EXAMPLES 2 to 6

By the process described in example 1, various compounds of formula I have been prepared, using the amines of formula II, as well as the reaction conditions indicated in the following table I, which gives also the melting point and the analytical data of the obtained compounds.

TABLE I

| Example | Amine of formula II | Temperature of reaction °C | Duration of reaction | Yield | Analysis | Melting point °C |
|---|---|---|---|---|---|---|
| 2 | p-methoxy-aniline | 20 | 16 hours | 90 | Found %:C:76.19;H:6.28; N:5.38<br>Calc.% :C:76.38;H:6.40; N:5.24 | 74 – 75° |
| 3 | p-amino-pyridine | 20 | instantaneous | 68 | product isolated as hydrobromide<br>Found %:C:56.10;H:4.9;N:8.79;Br:25.4<br>Calc.% :C:56.43;H:4.73;N:8.77;Br:25.03 | 305–310° |
| 4 | m-amino-pyridine | 55 | 1 hour 20 minutes | 80 | product isolated as hydrobromide<br>Found %:C:56.54;H:4.76;N:8.9;Br:24.8<br>Calc.%: C:56.43;H:4.73;N:8.77;Br:25.03 | 228–230° |
| 5 | o-methoxy-aniline | 20 | 48 hours | 53 | Found %: C:76; H:6.33; N:5.15<br>Calc. %: C:76.37; H:6.41; N:5.23 | 127–128° |
| 6 | m-methoxy-aniline | 20 | 72 hours | 50 | Found %: C:76.15; H:6.28; N:5.37<br>Calc. %: C:76.37; H:6.41; N:5.24 | 104–105° |

The new compounds of formula I may be used as intermediates in the preparation of known pharmaceutically active derivatives of 2-R-amino-tetralines of the formula:

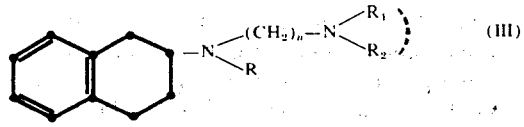

in which R has the above meanings, n = 1 to 4 and $R_1$ as well as $R_2$, which may be identical or different, represents an alkyl radical or form a nitrogenous heterocyclic ring with the attached nitrogen atom.

The compounds of formula (III) are active against heart arrhythmy.

The compounds of formula (III) may be prepared with high yields from the new compounds of formula (I) in only two steps, whereas the usual methods for preparing the same compounds of formula III require more steps.

The first step involves the reduction of the 2-R-amino-tetraline-1-ones of formula (I) into the corresponding 2-R-amino-tetralines of the formula

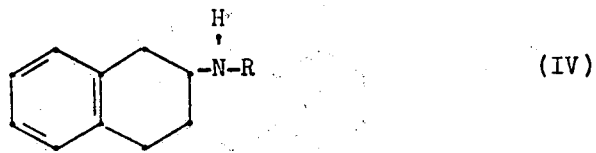

in which R has the above meanings.

Although the reduction of 2-R-amino-tetraline-1-ones is impossible by conventional methods, such as the Clemmensen method or the Wolff-Kishner method, it has been surprisingly found that said reduction can be made with a very good yield if the ketone is transformed by means of p-toluenesulfonylhydrazine into the p-toluenesulfonylhydrazone of the formula

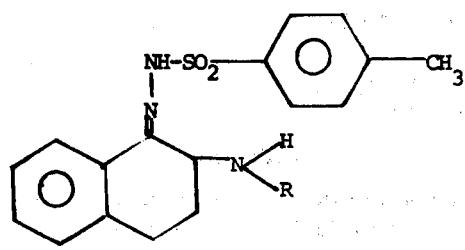

the crude p-toluenesulfonylhydrazone, without being isolated, being then reduced to the corresponding tetraline by means of catecholborane of the formula:

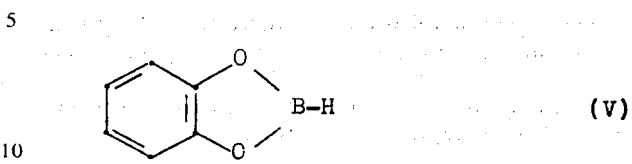

In the second step, a 2-R-amino-tetraline of the formula (IV) is reacted with sodium amide ($NaNH_2$) and with chlorinated amine of the formula

in which $n$, $R_1$ and $R_2$ have the above meanings, so as to obtain an active compound of formula III.

The following examples 7 to 12 illustrate the reduction of 2-R-amino-tetraline-1-ones of formula I into the corresponding 2-R-amino-tetralines of formula (IV).

EXAMPLE 7

2.37 grams (0.01 mol.) of 2-phenylaminotetralone (formula I: R = phenyl) are refluxed during 6 hours in 50 ml of ethanol, in the presence of one equivalent of tosylhydrazine. After the removal of the alcohol, 100 ml of alcohol-free chloroform are added to the residue (crude tosylhydrazone). After cooling to −10°C, 0.011 mol. of catecholborane are added and the reaction is allowed to take place during 30 minutes. 0.03 mol. of trihydrated sodium acetate are then added so as to initiate the decompositon of the intermediate addition product and the mixture is refluxed during 1 hour. After cooling, 100 ml of water are added and the pH is adjusted at 13. The obtained 2-phenylaminotetraline (yield: 80%) is extracted by means of chloroform and converted into hydrochloride. Melting point: 193° − 196°C.

EXAMPLES 8 to 11

By the process described in example 7, the compounds of formula IV listed in the following table have been prepared.

TABLE II

| Ex. | R | Melting point (hydrochlorides) °C | Analysis |
|---|---|---|---|
| 8 | OCH₃ (ortho) | 198–200 | Found:C:70.1;H:6.84;N: 4.71 % |
|   |   |   | Calc. C:70.45;H:6.96;N: 4.83 % |
| 9 | OCH₃ (meta) | 120–123 | Found:C:70.2;H:6.81;N: 4.8 % |
|   |   |   | Calc.:C:70.45;H:6.96;N: 4.83 % |

TABLE II -continued

| Ex. | R | Melting point (hydrochlorides) °C | Analysis | |
|---|---|---|---|---|
| 10 | ![benzene-OCH3] | 209-210 | Found:C:70.0;H:6.91;N: 4.7 | % |
| | | | Calc.:C:70.45;H:6.96;N: 4.83 | % |
| 11 | ![pyridyl] | 317 | Found:C:68.93;H:6.6 ;N: 10.7 | % |
| | | | Calc.:C:69.08;H:6.57;N: 10.74 | % |

What I claim is:

1. 2-R-amino-tetraline-1-ones of the formula:

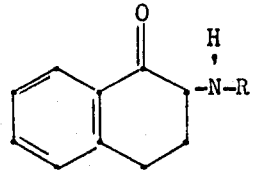

(I)

in which R represents a pyridyl or phenyl radical which may be substituted, in the ortho, meta or para position, by a methoxy group, as well as the acid addition salts thereof.

2. 2-phenylamino-tetraline-1-one.
3. 2-pyridylamino-tetraline-1-one.

* * * * *